United States Patent [19]

Meyer et al.

[11] 4,206,072
[45] Jun. 3, 1980

[54] BENZOXAZOLYL-PHENYL-STILBENES

[75] Inventors: Hans R. Meyer, Binningen; Kurt Burdeska, Basel, both of Switzerland

[73] Assignee: Ciba-Geigy Corporation, Ardsley, N.Y.

[21] Appl. No.: 956,314

[22] Filed: Oct. 31, 1978

[30] Foreign Application Priority Data

Nov. 10, 1977 [LU] Luxembourg .......................... 78484

[51] Int. Cl.² .......................................... C07D 263/56
[52] U.S. Cl. .............................. 252/301.24; 542/459; 8/648; 427/158
[58] Field of Search .................... 542/459; 252/301.24

[56] References Cited

U.S. PATENT DOCUMENTS

| 3,577,411 | 5/1971 | Liechti et al. | 542/459 |
| 3,682,900 | 8/1972 | Liechti et al. | 542/459 |
| 3,781,278 | 12/1973 | Siegrist et al. | 542/462 |
| 3,996,210 | 12/1976 | Fleck et al. | 542/459 |
| 4,014,870 | 3/1977 | Meyer | 542/459 |
| 4,032,558 | 6/1977 | Fleck et al. | 542/459 |

FOREIGN PATENT DOCUMENTS

| 806670 | 2/1969 | Canada. |
| 43-704568 | 3/1968 | Japan. |
| 44-697969 | 3/1969 | Japan. |
| 1418572 | 12/1975 | United Kingdom. |

Primary Examiner—Arthur P. Demers
Attorney, Agent, or Firm—Prabodh I. Almaula

[57] ABSTRACT

Benzoxazolyl-phenyl-stilbenes of the formula

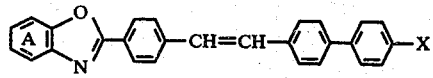

in which X is a carboxylic acid group or an ester or amide thereof, a phenyl sulphonate group or a sulphonamide group, a cyano group or alkylsulphonyl and the ring A can be substituted by alkyl having 1 to 4 C atoms, phenyl, chlorine, alkoxy having 1 to 4 C atoms, phenoxy, cyano, alkylsulphonyl having 1 to 4 C atoms, phenylsulphonyl or alkoxycarbonyl having 2 to 6 C atoms, a process for their manufacture as well as their use for the optical brightening are disclosed.

6 Claims, No Drawings

BENZOXAZOLYL-PHENYL-STILBENES

The present application relates to novel benzoxazolyl-phenyl-stilbenes, a process for their preparation and their use for the fluorescent brightening of natural and synthetic organic materials.

Benzoxazolyl-phenyl-stilbenes are already known from U.S. Pat. Nos. 3,850,914, 3,781,278 and 4,014,870 and also from Swiss Auslegeschrift 9052/69.

The novel benzoxazolyl-phenyl-stilbenes have the formula

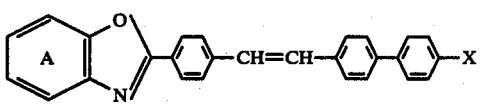
(1)

in which X is a carboxylic acid group or an ester or amide thereof, a phenyl sulphonate group or a sulphonamide group, a cyano group or alkylsulphonyl and the ring A can be substituted by alkyl having 1 to 4 C atoms, phenyl, chlorine, alkoxy having 1 to 4 C atoms, phenoxy, cyano, alkylsulphonyl having 1 to 4 C atoms, phenylsulphonyl or alkoxycarbonyl having 2 to 6 C atoms.

The ring A can be substituted by 1 to 3 of the indicated radicals, depending on the nature of the substituent.

The carboxylic acid group, esters and amides thereof and sulphonamide groups are the following radicals: —COOY, —CONY$_1$Y$_2$ or —SO$_2$NY$_1$Y$_2$, in which Y and Y$_1$ are hydrogen, alkenyl having 3 to 6 C atoms, cycloalkyl having 5 to 6 C atoms, phenyl or alkyl having 1 to 8, and preferably 1 to 4, C atoms, which can be substituted by alkoxy having 1 to 4 C atoms, hydroxyl, halogen, preferably chlorine, cyano, carboxyl, carbalkoxy having 2 to 5 C atoms, phenoxy, phenyl, tolyl, halogenophenyl, preferably chlorophenyl, or dialkylamino having a total of 2 to 6 C atoms, and Y$_2$ is hydrogen or alkyl having 1 to 6, and preferably 1 to 4, C atoms, and Y$_1$ and Y$_2$ together with the nitrogen atom are a piperidine or pyrrolidine ring or a morpholine ring which is unsubstituted or substituted by 1 or 2 methyl groups.

In ring A, two adjacent substituents can also form a trimethylene or tetramethylene radical.

Within the scope of the compounds of the formula (1), preferred compounds are those which have the formula

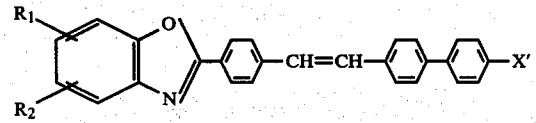
(2)

in which X' is cyano, alkylsulphonyl having 1 to 4 C atoms, phenoxysulphonyl, alkoxyalkoxycarbonyl having a total of 4 to 7 C atoms, carboxyl, alkoxycarbonyl having 2 to 6 C atoms, cyclohexyloxycarbonyl, phenoxycarbonyl or —CONY$_1$'Y$_2$' or —SO$_2$NY$_1$'Y$_2$', in which Y$_1$' and Y$_2$' are hydrogen or alkyl having 1 to 4 C atoms, R$_1$ is hydrogen, alkyl having 1 to 4 C atoms, phenyl, chlorine, alkoxy having 1 to 4 C atoms, phenoxy, cyano, alkylsulphonyl having 1 to 4 C atoms, phenylsulphonyl or alkpoxycarbonyl having 2 to 6 C atoms and R$_2$ is hydrogen, alkyl having 1 to 4 C atoms or chlorine.

Compounds of interest in practice are those which have the formula

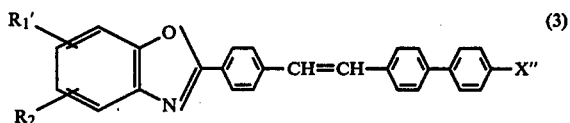
(3)

in which X" is cyano, carboxyl, alkoxycarbonyl having 2 to 6 C atoms or alkoxycarbonyl having a total of 4 to 7 C atoms, R$_1$' is hydrogen, alkyl having 1 to 4 C atoms, phenyl, alkoxycarbonyl having 2 to 6 C atoms, alkoxy having 1 to 4 C atoms or chlorine and R$_2$ is hydrogen, alkyl having 1 to 4 C atoms or chlorine, compounds which have the formula

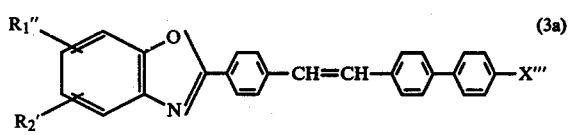
(3a)

in which X''' is cyano, carboxyl or alkoxycarbonyl having 2 to 6 C atoms, R$_1$'' is hydrogen, alkyl having 1 to 4 C atoms, phenyl, alkoxycarbonyl having 2 to 6 C atoms, chlorine or methoxy and R$_2$' is hydrogen, methyl, ethyl or chlorine, or compounds which have the formula

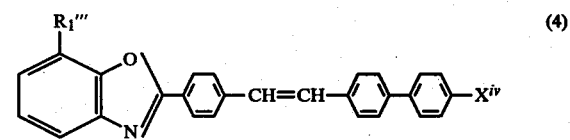
(4)

in which X$^{iv}$ is cyano or alkoxycarbonyl having 2 to 5 C atoms and R$_1$''' is alkyl having 1 to 4 C atoms or methoxy.

When used on polyester, compounds of the formulae (3), (3a) and (4) produce white effects which are particularly powerful and fast to light.

The compounds of the formula (1) can be prepared in a manner known per se. Thus, those of the formulae (3), (3a) and (4) can be prepared by reacting a compound of the formula

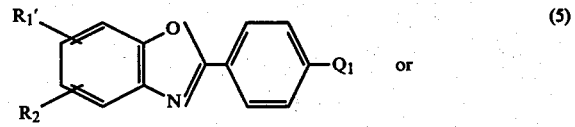
(5)

or

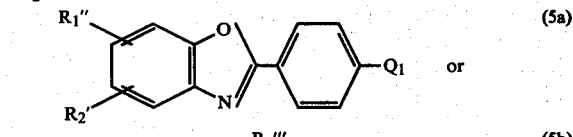
(5a)

or

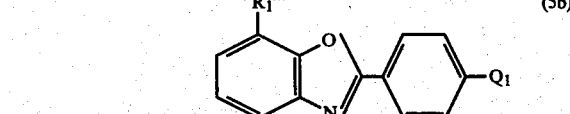
(5b)

with a compound of the formula

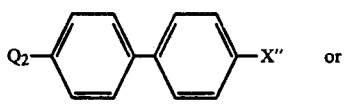 (6)

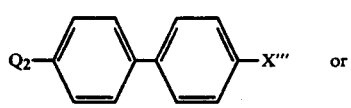 (6a)

 (6b)

in which formulae $R_1'$, $R_1''$, $R_1'''$, $R_2$, $R_2'$, $X''$, $X'''$ and $X^{iv}$ are as defined above and one of the symbols $Q_1$ and $Q_2$ is a —CHO group and the other is a grouping of the formula

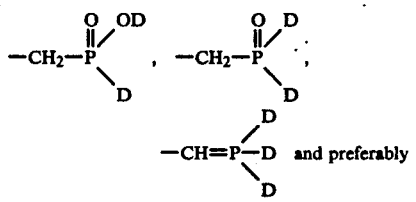 and preferably in which D is an unsubstituted or substituted alkyl, aryl, cycloalkyl or aralkyl radical, in the presence of a strong base.

This method of preparation is advantageously carried out in inert solvents. Examples of such solvents are hydrocarbons, which can be chlorinated, such as toluene and xylene, chlorobenzene or dichlorobenzene, or alcohols, such as methanol, ethanol, isopropanol or butanol, glycols, glycol ethers such as 2-methoxyethanol, hexanols, cyclohexanol and cyclooctanol and also ethers such as diisopropyl ether, tetrahydrofuran and dioxan, and dimethylsulphoxide, formamide, tetramethylurea and N-methylpyrrolidone. Polar organic solvents such as dimethylformamide and dimethylsulphoxide are particularly suitable. Some of the reactions can also be carried out in aqueous solution.

The temperature at which the reaction is carried out can vary within wide limits. It is determined by (α) the stability of the solvent used towards the reactants, especially towards the strongly basic alkali metal compounds, (β) by the reactivity of the reactants undergoing condensation and (γ) by the effectiveness of the solvent/base combination as a condensing agent.

In practice, accordingly, the temperature can generally be between about 10° and 100° C., especially if dimethylformamide or dimethylsulphoxide is used as the solvent. The preferred temperature range is from 20° to 60° C.

Strongly basic alkali metal compounds are, in particular, the hydroxides, amides and alcoholates (preferably of alcohols containing 1 to 4 carbon atoms) of the alkali metals, those of lithium, sodium and potassium being of predominant interest for economic reasons. However, in principle and in special cases, alkali metal sulphides and alkali metal carbonates, aryl-alkali metal compounds, for example phenyl-lithium, or strongly basic amines (including ammonium bases), for example trialkylammonium hydroxides, can also be used successfully.

The compounds of the formula (1) in which $X = X'$, i.e. a carboxylic acid ester group, a carboxamide group or a nitrile group, can also be prepared by reacting a o-aminophenol of the formula

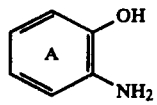 (7)

preferably in an inert high-boiling solvent, with a compound of the formula

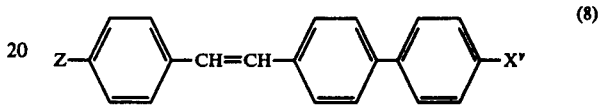 (8)

in which formulae the ring A can be substituted as indicated above, $X'$ is as defined above and Z is a carboxyl group or a functional derivative, preferably a chloride.

Compounds of the formula (1) in which X is a carboxylic acid group or carboxamide group can also be prepared by reacting a Schiff's base of the formula

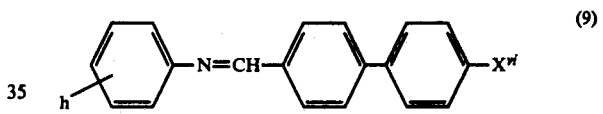 (9)

in which $X^{ri}$ is carboxyl or —$CONY_1Y_2$, in which $Y_1$ and $Y_2$ are as defined above, and h is hydrogen or chlorine, with a methyl compound of the formula

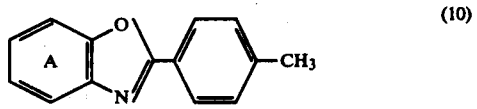 (10)

in which the ring A can be substituted as indicated above, in the presence of a strongly basic alkali metal compound in a strongly polar, neutral to basic organic solvent.

Compounds of the formula (1) in which X is a phenyl sulphonate group or sulphonamide group can be prepared by reacting a compound of the formula

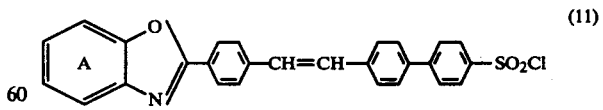 (11)

in which the ring A can be substituted as indicated above, in a manner known per se, if appropriate in the presence of a base, with an alcohol or an amine.

Compounds of the formula (1) in which X is a carboxamide group can also be prepared by reacting a compound of the formula

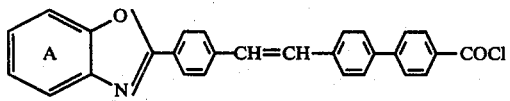 (12)

in which the ring A can be substituted as indicated above, with an amine in a manner known per se.

Compounds of the formula (1) in which X is alkylsulphonyl can be prepared by reducing a compound of the formula (11) in a manner known per se, for example with sodium sulphite, to give the sulphinate and alkylating the latter with the conventional alkylating agents, such as dialkyl sulphates, alkyl halides, arylsulphonic acid esters or dialkylmethanephosphonates and the like.

The starting materials of the formulae (5) to (11) are known or are prepared analogously to processes known per se. The preparation of novel typical starting materials is described in the examples.

As mentioned, the reaction of compounds of the formula (9) with those of the formula (10) is carried out in the presence of a strongly polar, neutral or alkaline organic solvent. This must be free from atoms, especially hydrogen atoms, which are replaceable by alkali metals. In practice, such solvents are, in particular, dialkylamides of formic acid and of phosphoric acid and also tetraalkylureas, in which alkyl is a lower alkyl group containing 1 to 4 carbon atoms, especially a methyl group. Important representatives of such solvents are: diethylformamide, hexamethylphosphoric acid triamide, tetramethylurea and especially dimethylformamide. Solvent mixtures can also be used.

Furthermore, as has been mentioned, a strongly basic alkali metal compound is required for the reaction. Depending on the nature of the solvent used and on the reactivity of the anil employed, alkali metal compounds suitable for this purpose are specific sodium alcoholates, such as sodium t-butylate and sodium methylate, and especially potassium compounds having the composition

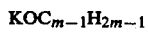

in which m is an integer from 1 to 6, preferably 2 to 6, for example potassium hydroxide or especially potassium tertiary butylate. In the case of alkali metal alcoholates, the reaction must be carried out in a virtually anhydrous medium, whilst in the case of potassium hydroxide a low water content of up to about 15% (for example content of water of crystallisation) is still permissible. Potassium hydroxide or sodium t-butylate are sometimes advantageously used in combination with hexamethylphosphoric acid triamide at relatively high temperature, for example at 100° to 130° C. Of course, it is also possible to carry out the reaction with mixtures of such bases.

Particularly good yields are obtained when potassium t-butylate is used in 1 to 6 times, and preferably 2 to 4 times, the equivalent amount.

The reaction can generally be carried out at temperatures in the range between about 10° and 150° C. and preferably at 40° to 70° C.

The novel compounds defined above exhibit a more or less pronounced fluorescence in solution or dispersion. They can be used for the fluorescent brightening of a wide variety of synthetic, regenerated man-made or natural organic materials or substances which contain such organic materials.

Without any restriction being implied by the following classification, examples of organic materials which can undergo fluorescent brightening are: I. Synthetic organic materials of high molecular weight:

(a) Polymerisation products based on organic compounds containing at least one polymerisable carbon-carbon double bond, i.e. their homopolymers or copolymers as well as their after-treatment products, for example crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds (for example acrylates, acrylic acid, acrylonitrile, acrylamides and their derivatives or their methacrylic analogues), on olefin hydrocarbons (for example ethylene, propylene, styrenes or dienes and also ABS polymers) and polymers based on vinyl and vinylidene compounds (for example vinyl chloride, vinyl alcohol and vinylidene chloride), (b) Polymerisation products which can be obtained by ring opening, for example polyamides of the polycaprolactam type, and also polymers which are obtainable either by polyaddition or by polycondensation, such as polyethers or polyacetals, (c) Polymerisation products or precondensates based on bifunctional or polyfunctional compounds with condensable groups, the homocondensation and co-condensation products, and after-treatment products thereof, for example polyesters, in particular saturated polyesters (for example polyesters of ethylene glycol/terephthalic acid) or unsaturated polyesters (for example maleic acid/dialcohol polycondensates and their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, the precondensates and analogues thereof, polycarbonates and silicones, (d) Polyaddition products, such as polyurethanes (crosslinked and uncrosslinked) and epoxide resins.

The organic materials which are to undergo fluorescent brightening can be in the most diverse states of processing (raw materials, semi-finished goods or finished goods). On the other hand, they can be in the form of structures of the most diverse shapes, for example predominantly three-dimensionally expanded structures, such as sheets, profiles, injection mouldings, various machined articles, chips, granules or foams, and also predominantly two-dimensional structures, such as films, foils, lacquers, coverings, impregnations and coatings, or predominantly one-dimensional bodies, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

Fibrous materials can be, for example, in the form of endless filaments (stretched or unstretched), staple fibres, flocks, hanks, textile filaments, yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be subjected to fluorescent brightening according to the invention, this is advantageously effected in an aqueous medium in which the compounds in question are present in a finely divided form (suspensions, so-called micro-dispersions, or optionally solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperatures of about 20° to 140° C., for example at the boiling point of the bath or near it (about 90° C.). Solutions or emulsions in organic solvents can also be used for the finishing according to the invention of textile substrates, as is practised in the dyeing industry in so-called solvent dyeing (pad-thermo fixation, or exhaust dyeing processes in dyeing machines).

The novel fluorescent brightening agents according to the present invention can further be added to, or incorporated in, the materials before or during their shaping. Thus they can, for example, be added to the compression moulding composition or injection moulding composition during the manufacture of films, sheets (for example incorporated in polyvinyl chloride in a roll mill at elevated temperature) or mouldings.

If the shaping of man-made synthetic or regenerated man-made organic materials is effected by spinning processes or from spinning solutions/melts, the fluorescent brightening agents can be applied by the following processes:
 addition to the starting substances (for example monomers) or intermediates (for example precondensates or prepolymers), i.e. before or during the polymerisation, polycondensation or polyaddition,
 sprinkling in powder form on polymer chips or granules for spinning solutions/melts,
 bath dyeing of polymer chips or granules for spinning solutions/melts,
 metered addition to spinning melts or spinning solutions, and
 application to the spun tow before stretching.

The novel fluorescent brightening agents according to the present invention can, for example, also be employed in the following use forms:
 (a) In mixtures with dyes (shading) or pigments (coloured pigments or especially, for example, white pigments), or as an additive to dye baths, printing pastes, discharge pastes or reserve pastes, or for the after-treatment of dyeings, prints or discharge prints,
 (b) In mixtures with carriers, wetting agents, plasticisers, swelling agents, antioxidants, light stabilisers, heat stabilisers and chemical bleaching agents (chlorite bleach or bleaching bath additives),
 (c) In mixtures with crosslinking agents or finishing agents (for example starch or synthetic finishes) and in combination with a wide variety of textile finishing processes, especially synthetic resin finishes (for example creaseproof finishes such as "wash-and-wear", "permanent-press" or "no-iron"), as well as flameproof finishes, soft-handle finishes, anti-soiling finishes or antistatic finishes, or antimicrobial finishes,
 (d) Incorporation of the fluorescent brightening agents into polymeric carriers (polymerisation, polycondensation or polyaddition products) in dissolved or dispersed form the use, for example, in coating agents, impregnating agents or binders (solutions, dispersions and emulsions) for textiles, non-wovens, papers and leather,
 (e) As additives to master batches,
 (f) As additives to a wide variety of industrial products in order to render these more marketable (for example improving the appearance of soaps, detergents, pigments),
 (g) In combination with other fluorescent brightening substances,
 (h) In spinning bath preparations, i.e. as additives to spinning baths which are used for improving the slip for the further processing of synthetic fibres, or from a special bath before the stretching of the fibre,
 (i) As scintillators for various purposes of a photographic nature, for example for electrophotographic reproduction or supersensitising and
 (j) depending on the substitution, as laser dyes.

If the brightening process is combined with textile treatment or finishing methods, the combined treatment can in many cases advantageously be carried out with the aid of appropriate stable preparations which contain the fluorescent brightener compounds in such a concentration that the desired white effect is achieved.

In certain cases, the fluorescent brightening agents are made fully effective by an after-treatment. This can be, for example, a chemical treatment (for example acid treatment), a thermal treatment (for example heat) or a combined chemical/thermal treatment. Thus, for example, the appropriate procedure to follow for the fluorescent brightening of a number of fibre substrates, for example polyester fibres, with the fluorescent brightening agents of the present invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or combined in a single operation.

The amount of the novel fluorescent brightening agents to be used according to the invention, based on the material to be subjected to fluorescent brightening, can vary within wide limits. A marked and lasting effect can be obtained even with very small amounts, in certain cases, for example, amounts of 0.0001 percent by weight. But it is also possible to use amounts of up to about 0.8 percent by weight and in some cases of up to about 2 percent by weight. For most practical purposes, it is preferable to use amounts between 0.0005 and 0.5 percent by weight.

For various reasons it is often advantageous not to use the fluorescent brighteners by themselves, i.e. pure, but in admixture with a wide variety of assistants and extenders, for example anhydrous sodium sulphate, sodium sulphate decahydrate, sodium chloride, sodium carbonate, alkali metal phosphates, such as sodium or potassium orthophosphate, sodium or potassium pyrophosphate and sodium or potassium tripolyphosphates, or alkali metal silicates.

In the examples, percentages are always by weight. Melting points and boiling points are uncorrected, unless stated otherwise. The melting points are usually extremely unsharp.

EXAMPLE 1

2.2 g of sodium methylate are added to a solution of 10.4 g of the phosphonate of the formula

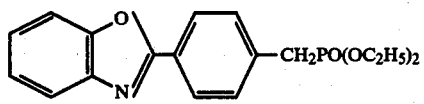
(100)

and 8.0 g of the aldehyde of the formula

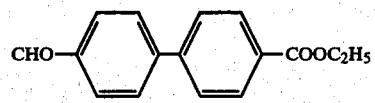
(101)

in 100 ml of anhydrous dimethylformamide, with stirring and whilst passing in a gentle stream of nitrogen. The temperature is allowed to rise to 40° C. and the mixture is stirred for 2 hours at this temperature. After cooling in an icebath, 20 ml of water are added and the precipitate formed is filtered off with suction, washed with methanol and with water until neutral and dried in vacuo. This yields 11.3 g (84% of theory) of the compound of the formula

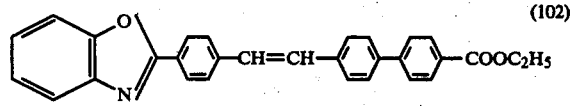
(102)

which after recrystallisation from dimethylformamide and o-dichlorobenzene is isolated as pale yellow crystals with a melting point of 239° C. (unsharp).

The compounds of the general formula

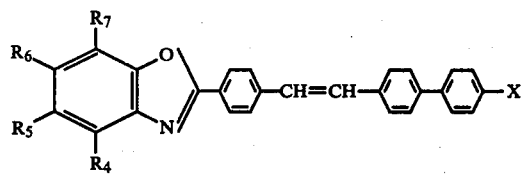
(103)

listed in Table I are obtained in a similar manner from the corresponding phosphonates and aldehydes.

TABLE I

| Formula | $R_4$ | $R_5$ | $R_6$ | $R_7$ | X | Melting point °C. |
|---------|-------|-------|-------|-------|---|-------------------|
| (104) | H | H | H | H | $COOCH_3$ | 292 |
| (105) | H | $CH_3$ | H | $CH_3$ | $COOCH_3$ | 238 |
| (106) | H | $COOCH_3$ | H | H | $COOCH_3$ | 264 |
| (107) | H | $C(CH_3)_3$ | H | H | $COOCH_3$ | 258 |
| (108) | H | $COOCH_3$ | H | H | $COOC_2H_5$ | 212 |
| (109) | H | $CH_3$ | H | $CH_3$ | $COOC_2H_5$ | 188 |
| (110) | H | $C(CH_3)_3$ | H | H | $COOC_2H_5$ | 190 |
| (111) | H | H | Cl | Cl | $COOC_2H_5$ | 230 |
| (112) | H | H | H | H | CN | 273 |
| (113) | H | $C(CH_3)_3$ | H | H | CN | 286 |
| (114) | H | H | H | H | $COOCH(CH_3)_2$ | 284 |
| (115) | H | H | H | Phenyl | $COOC_2H_5$ | 233 |
| (116) | H | H | H | Cl | $COOC_2H_5$ | 235 |
| (117) | $CH_3$ | H | H | H | $COOC_2H_5$ | 180 |
| (118) | $CH_3$ | $CH_3$ | H | H | $COOC_2H_5$ | 212 |
| (119) | H | H | H | $C_3$ | $COOC_2H_5$ | 151 |
| (120) | $CH_3$ | H | H | H | CN | 241 |
| (130) | H | H | H | H | $COOC_3H_7$ | 266 |
| (131) | H | H | H | $CH_3$ | CN | 222 |
| (132) | H | H | H | H | $COO(CH_2)_2OCH_3$ | 231 |
| (133) | H | H | H | $CH_3$ | $COOCH_3$ | 219 |
| (134) | H | H | H | $C_2H_5$ | $COOC_2H_5$ | 190 |
| (135) | H | H | H | $OCH_3$ | $COOC_2H_5$ | 218 |

The aldehyde used as the starting material for the compound of the formula (104) is prepared as follows: 208.6 g of the compound of the formula

(121)

(German Offenlegungsschrift 2,309,614) are added to a solution of 123.4 g of hexamethylenetetramine in 800 ml of chloroform, at the reflux temperature, and the mixture is stirred for 1 hour at this temperature. The hexamethylenetetramine salt, which has separated out as a thick precipitate after a few minutes, is filtered off with suction at 0° C., washed with chloroform and dried (306.0 g with a melting point of 196° C. with decomposition). This salt is stirred in 850 ml of glacial acetic acid and 850 ml of water for 2 hours under reflux. The product which has precipitated on cooling in an icebath is filtered off with suction, washed with water until neutral and dried in vacuo at 70° C. This yields 138.2 g (72% of theory) of the compound of the formula

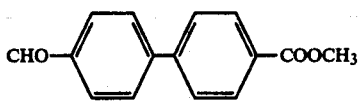
(122)

which after recrystallisation from alcohol melts at 108° C.

The esters of other alcohols, for example the ethyl ester of the formula (101) which has a melting point of 61° C. and is required for the preparation of the compound of the formula (102), are obtained in the same way. The corresponding n-propyl ester melts at 48° C. and the methoxyethyl ester melts at 68° C.

The 2-(4'-diethylphosphonomethyl-phenyl)-7-chlorobenzoxazole required as the starting material for the preparation of the compound (116) is prepared as follows:

158.5 g of 2-(4'-chloromethylphenyl)-7-chlorobenzoxazole (prepared by a condensation reaction of 2-amino-6-chlorophenol with 4-chloromethyl-benzoyl chloride with subsequent cyclisation in o-dichlorobenzene in the presence of p-toluenesulphonic acid, melting point 141° to 142° C.) are heated with 400 ml of triethyl phosphite to 155° C. in the course of 2 hours and the mixture is then stirred for a further 7 hours at 155° to 158° C. After cooling to 90° C., the excess triethyl phosphite is distilled off in vacuo. The reaction product, which is still oily, is stirred into 1,000 ml of petroleum ether and crystallisation takes place after a short time. The product is filtered off, washed with petroleum ether and dried. This yields 210 g (97% of theory) of 2-(4'-diethylphosphonomethylphenyl)-7-chloro-benzoxazole with a melting point of 92° to 93° C.

The phosphonates which are required for the preparation of the other compounds listed in Table I are obtained in an analogous manner.

EXAMPLE 2

32.1 g of the crude product of the formula

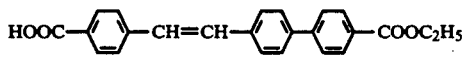
(200)

are stirred in 75 ml of thionyl chloride for 3 hours under reflux, after which time the evolution of hydrogen chloride has ceased. The reaction mixture is diluted with 125 ml of carbon tetrachloride and the product which has precipitated is filtered off with suction, washed with 1:1 carbon tetrachloride/thionyl chloride and dried in vacuo at 70° C; yield 19.5 g.

11.7 g of the resulting acid chloride of the formula

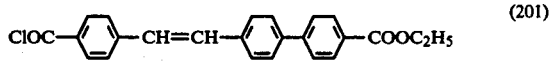
(201)

(melting point of a sample crystallised from xylene=239° C.) are heated with 3.7 g of 2-amino-4-methyl-phenol in 50 ml of trichlorobenzene at 150° C. until the evolution of hydrogen chloride has ceased (about ¼ hour). After adding 0.5 g of boric acid and 0.5 g of quinoline, the reaction mixture is heated to the boil and the water formed is distilled off, together with a little trichlorobenzene, in the course of 3 hours. The solution is allowed to cool and is diluted with 50 ml of methanol and the precipitate is filtered off with suction, washed with methanol and dried. After boiling thoroughly with 150 ml of dimethylformamide, filtering at room temperature and drying the filter residue in vacuo at 100° C., this yields 10.6 g of the compound of the formula

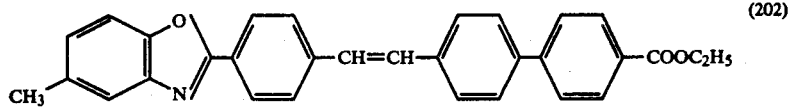
(202)

with a melting point of 244° C. (unsharp), after recrystallisation from o-dichlorobenzene and dimethylformamide.

The compound of the formula (200) required as the starting material is prepared as follows:

51.7 g of 90% terephthalaldehydic acid and 117.0 g of the compound of the formula

(203)

with a melting point of 58° C. (preparation according to German Offenlegungsschrift 2,309,614 for the corresponding methyl ester) are dissolved in 500 ml of dimethylformamide and 104.4 g of potassium t-butylate are introduced in portions, with stirring and whilst passing nitrogen over the mixture. The temperature is allowed to rise to 45° C. and the reaction mixture is stirred for 2 hours at this temperature. After cooling in an ice bath, 1,000 ml of water are added and the mixture is acidified with 80 ml of concentrated hydrochloric acid. The precipitate is filtered off with suction, washed with water until neutral and dried in vacuo at 100° C. This yields 107.6 g of crude product, which when recrystallised from o-dichlorobenzene and pyridine melts at 297° C. (unsharp).

EXAMPLE 3

18.0 g of potassium t-butylate are introduced in portions into a solution of 9.5 of 5,7-dimethyl-2-(p-tolyl)-benzoxazole and 12.1 g of the anil of the formula

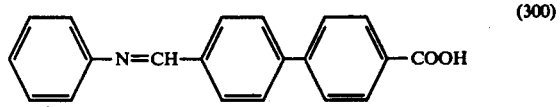
(300)

in 110 ml of anhydrous dimethylformamide, at 60° C., with stirring and slight cooling and whilst passing nitrogen over the mixture, a violet coloration being obtained. This temperature is maintained for 1 hour and the mixture is cooled, 220 ml of water are added and the resulting mixture is acidified with about 21 ml of concentrated hydrochloric acid. The product which has precipitated is filtered off with suction, washed repeatedly with water and boiled thoroughly with 100 ml of dimethylformamide. After cooling, filtering off with suction, washing with dimethylformamide and drying in vacuo, this yields 7.3 g (41% of theory) of the compound of the formula

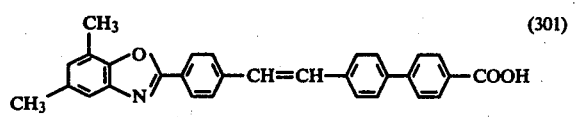 (301)

For further purification, the product can be recrystallised from a large amount of dimethylformamide, pale yellow crystals with a melting point of >360° C. being obtained.

The compounds of the general formula

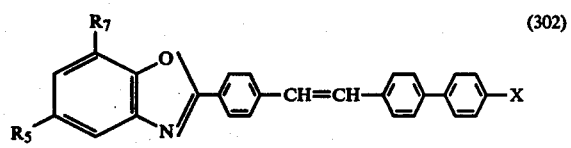 (302)

listed in Table II are obtained in a similar manner.

TABLE II

| Formula | $R_5$ | $R_7$ | X | Melting point °C. |
|---------|-------|-------|---|-------------------|
| (303)   | H     | H     | COOH | >360 |
| (304)   | $CH_3$ | $CH_3$ | $CONHC_6H_5$ | 300 |

The anil of the formula (300) required as the starting material is prepared as follows:

30 ml of concentrated hydrochloric acid are added dropwise to a solution of 14.4 g of the compound of the formula (122) in 30 ml of dioxan, with stirring, at 60° C. The mixture is stirred for 8 hours under reflux and is allowed to cool to room temperature and the resulting suspension is filtered. After washing the material on the filter with water and methanol and drying in vacuo at 100° C., 12.75 g (94% of theory) of the compound of the formula

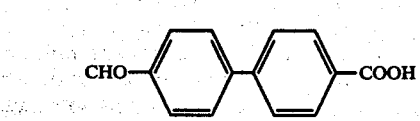 (305)

are obtained.

A sample purified by recrystallisation from ethylene glycol monomethyl ether and sublimation under a high vacuum at 230° C. has a melting point of 314° C.

11.3 g of the compound thus obtained and 5.1 g of aniline are stirred for ½ hour in 50 ml of ethylene glycol monomethyl ether under reflux. The aldehyde goes into solution and the yellow anil precipitates. The latter is filtered off with suction at 0° C., washed with ethylene glycol monomethyl ether and dried in vacuo at 100° C. Yield 13.5 g (90% of theory).

A sample purified by recrystallisation from o-dichlorobenzene and sublimation has a melting point of 263° C.

EXAMPLE 4

5.00 g of finely powdered sulphonic acid chloride of the formula

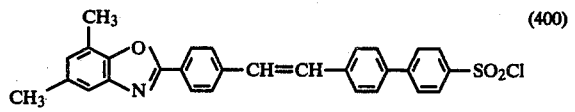 (400)

(German Offenlegungsschrift 2,525,681) are added to a solution of 0.76 g of sodium methylate and 1.88 g of phenol in 20 ml of pyridine and the mixture is stirred for 1 hour at room temperature, for ½ hour at 80° C. and for ½ hour under reflux. After cooling, the mixture is filtered and the residue is washed with methanol and dried. The product is recrystallised from chlorobenzene and this yields 2.62 g (47% of theory) of the compound of the formula

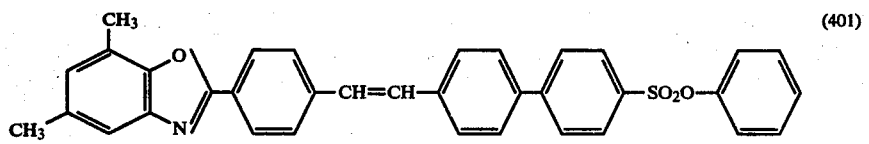 (401)

in the form of small pale yellow leaves with a melting point of 236° C.

EXAMPLE 5

15.0 g of the sulphonyl chloride of the formula (400) are dissolved in 150 ml of boiling chlorobenzene. After cooling to 80° C., 9.7 ml of a 70% aqueous solution of ethylamine are added dropwise to the fine suspension and the mixture is stirred for 6 hours at this temperature. The mixture is filtered at room temperature and the residue is washed with chlorobenzene and alcohol and dried in vacuo at 100° C. This yields 14.0 g of a pale yellow product of the formula

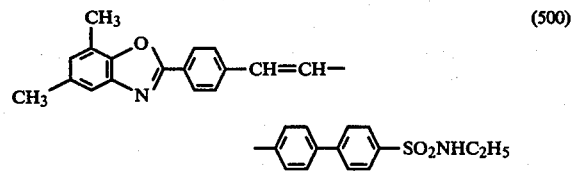 (500)

which after recrystallisation from anisole and dimethylformamide melts at 246° C.

The compound of the formula

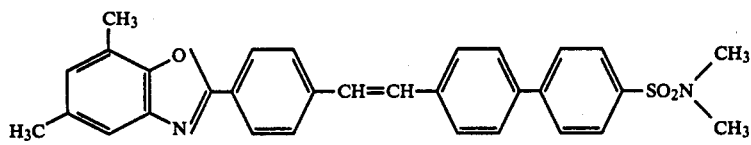

which after recrystallisation from chlorobenzene and dimethylformamide melts at 271° C., is obtained in an analogous manner by using a 33% alcoholic solution of dimethylamine in place of ethylamine.

EXAMPLE 6

A solution of 23.0 g of 96% pure sodium sulphite in 60 ml of water is added to a suspension of 25.0 g of finely powdered sulphonic acid chloride of the formula (400) in 500 ml of dioxan, at 90° C. 10.9 ml of a 30% aqueous solution of sodium hydroxide are gradually added dropwise at this temperature in such a way that the pH value is always 8.5 to 9. After stirring for 12 hours at 90° to 95° C., the reaction mixture is cooled and filtered with suction and the residue is repeatedly washed with dioxan and water and dried. This yields 20.1 g of the sulphinate of the formula (600)

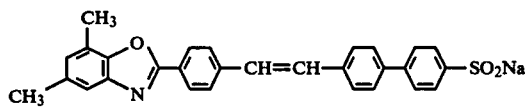

The compound can be recrystallised from dimethylsulphoxide. Melting point >360° C.

9.8 g of the crude sulphinate, 1.77 g of sodium bicarbonate and 0.56 ml of triethylamine are stirred in 60 ml of dimethyl methanephosphonate for 3 hours under reflux. The mixture is allowed to cool, 20 ml of water are added, the resulting mixture is filtered and the residue is washed repeatedly with methanol and water. The dried product is recrystallised from chlorobenzene. 3.3 g of the compound of the formula

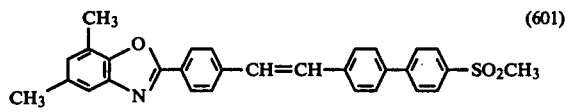

are obtained.

After chromatography on aluminium oxide by means of benzene/methylene chloride, 1:1 to 9:1, pale yellow crystals with a melting point of 250° C. (unsharp) are obtained.

EXAMPLE 7

4.2 g of the compound of the formula

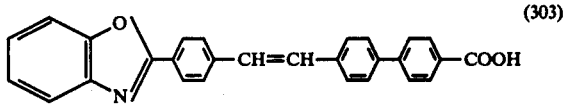

are stirred in 20 ml of thionyl chloride and 1.5 g of dimethylformamide are added dropwise to the suspension. The mixture is heated for 4 hours under reflux and the excess solvent is stripped off in vacuo at 50° C. The residue is stirred in 20 ml of alcoholic 33% dimethylamine solution for ½ hour at room temperature and for 1 hour under reflux. After cooling to room temperature, the product is filtered off with suction, washed with alcohol and dried. This yields 3.2 g of the compound of the formula

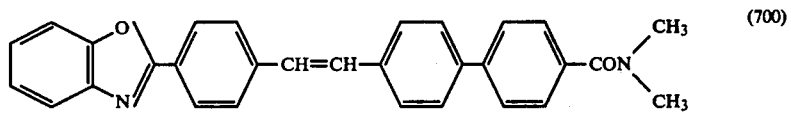

which after recrystallisation from o-dichlorobenzene and dimethylformamide melts at 288° C.

If a 70% aqueous solution of ethylamine is used in place of dimethylamine, the compound of the formula

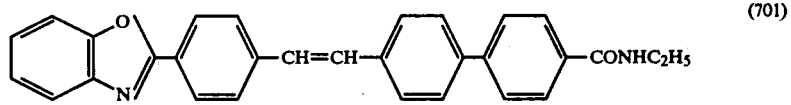

with a melting point of 276° C. is obtained.

The carboxylic acid of the formula (303), which is required as the starting material, is obtained as follows:

10.4 g of the phosphonate of the formula

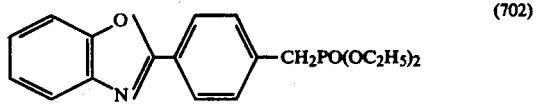

and 7.9 g of the aldehyde of the formula (305) are dissolved in 100 ml of hot dimethylformamide. After cooling to 40° C., 4.3 g of sodium methylate are added, whilst passing nitrogen over the mixture, and the mixture is stirred for 2 hours at 45° C. After cooling in an ice bath, 200 ml of water and then 10 ml of concentrated hydrochloric acid are added. The precipitate is filtered off with suction, washed repeatedly with water and methanol, dried, recrystallised from N-methylpyrrolidone and washed with alcohol. After drying, 8.4 g of the yellowish, sparingly soluble compound of the formula (303) with a melting point of >360° C. are obtained.

EXAMPLE 8

The compounds of the formula

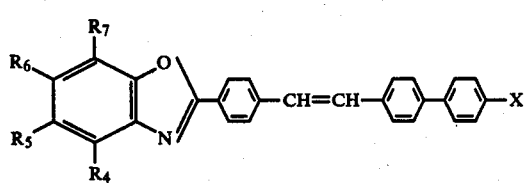
(800)

listed in Table III below can be prepared according to Example 1 or 2.

TABLE III

| Formula | $R_4$ | $R_5$ | $R_6$ | $R_7$ | X |
|---|---|---|---|---|---|
| (801) | H | H | H | $OC_6H_5$ | $COOC_2H_5$ |
| (802) | H | H | H | $OCH_3$ | CN |
| (803) | H | $SO_2C_2H_5$ | H | H | $COOC_2H_5$ |
| (804) | H | H | $OCH_3$ | CN | $COOC_2H_5$ |
| (805) | H | H | H | $-\underset{\underset{CH_3}{\mid}}{CH}-CH_2CH_3$ | $COOC_2H_5$ |
| (806) | H | H | H | $-CH\underset{CH_3}{\overset{CH_3}{<}}$ | $COOC_2H_5$ |
| (807) | H | H | H | $-C(CH_3)_3$ | $COOCH_3$ |
| (808) | H | H | H | $CH_3$ | $COO(CH_2)_2OCH_3$ |

EXAMPLE 9

Polyester fabric (for example ®Dacron) is padded at room temperature with an aqueous dispersion which contains, per liter, 0.5, 1 or 2 g of a fluorescent brightening agent of the formula (102), (104), (109), (112), (115), (116) to (120), (131) to (134) or (135) and also 1 g of an adduct of about 8 mols of ethylene oxide and 1 mol of p-tert.-octylphenol. The liquor pick-up is 80%. The fabric is dried for 10 minutes at 80° C. and is then heated for 30 seconds at 220° C.

The fabric treated in this way displays a powerful white effect with good fastness to light.

EXAMPLE 10

Modified polyester fabric (for example ®Dacron 64) is padded at room temperature with an aqueous dispersion which contains, per liter, 0.5, 1 or 2 g of a fluorescent brightening agent of the formula (102), (104), (109), (112), (115), (116), (118), (119), (120), (131) to (134) or (135) and 0.1 g of an adduct of 2 to 5 mols of ethylene oxide and 1 mol of p-tert.-octylphenol. The liquor pick-up is 80%. The fabric is dried for 10 minutes at 80° C., heated for 30 seconds at 220° C. and then washed for 10 minutes at 95° C., using a liquor ratio of 1:30, in a wash liquor containing 5 g of soap and 2 g of sodium carbonate per liter, rinsed for 30 seconds in running cold water and dried at 180° to 190° C. with an iron.

The fabric treated in this way displays a powerful white effect with good fastness to light.

EXAMPLE 11

1,000 g of polyester granules of the ethylene glycol terephthalate type, containing 0.5% of $TiO_2$ (anatase type) are mixed with 1 g of a compound of the formula (102) in a Rhönrad mixer and the granules treated in this way are spun to a multifilament in an extruder spinning installation at 280° C. The resulting filaments display an excellent white effect with good fastness to light.

Similarly good effects are obtained when a fluorescent brightening agent of the formula (104) to (113), (115), (116) to (120), (131) to (134), (202), (301) or (303) is used in place of the fluorescent brightening agent of the formula (102).

EXAMPLE 12

An intimate mixture of 65 parts of polyvinyl chloride (suspension type), 32 parts of dioctyl phthalate, 3 parts of an epoxidised soya bean oil, 1.5 parts of a stabiliser (for example ®Irgastab BC 26), 0.5 part of a costabiliser (for example ®Irgastab CH 300), 5 parts of $TiO_2$ (rutile type) and 0.1 part of a compound of the formula (102) is rolled out on a calender at 150° C. to give a film. The resulting film displays a powerful white effect with good fastness to light.

Similarly good effects are obtained when a fluorescent brightening agent of the formula (104), (105), (107), (109), (111) to (120), (130), (131), (401) or (500) is used in place of the fluorescent brightening agent of the formula (102).

EXAMPLE 13

10,000 g of a polyamide which has been prepared in a known manner from hexamethylenediamine adipate and is in chip form are mixed with 30 g of titanium dioxide (rutile modification) and 5 g of the compound of the formula (102), (104), (112), (115), (117) to (120) or (303) in a tumbler for 12 hours. The chips treated in this way are melted in a kettle, heated with oil or diphenyl vapour to 300° to 310° C., after displacing the atmospheric oxygen by steam, and the melt is stirred for half an hour. The melt is then extruded under a nitrogen pressure of 5 atmospheres through a spinneret and the cooled filament spun in this way is wound up on a spinning bobbin. The resulting filaments have a good white effect.

If a polyamide prepared from ε-caprolactam is used in place of a polyamide prepared from hexamethylenediamine adipate, similarly good results are obtained.

EXAMPLE 14

300 g of polystyrene granules and 1.5 g of anatase titanium dioxide in 900 ml of dimethylformamide are processed to a homogeneous viscous mass using a high-speed stirrer. 10 g of the casting composition thus obtained are mixed intimately with 5 mg of the fluorescent brightening agent of the formula (109) or (113) by stirring in a glass jar.

The resulting casting composition is cast on a glass plate, drawn out to a film with a metal rod and dried at room temperature with moderate ventilation.

The resulting film displays a powerful white effect.

EXAMPLE 15

1,200 g of acetylcellulose (36%) granules and 6.2 g of anatase titanium dioxide in 1,400 ml of acetone are processed to a homogeneous viscous mass using a high-speed stirrer. 10 g of the casting composition thus obtained are mixed intimately with 5 mg of the fluorescent brightening agent of the formula (109) or (401) by stirring in a glass jar.

The resulting casting composition is cast on a glass plate, drawn out to a film with a metal rod and dried at room temperature with moderate ventilation.

The resulting film displays a powerful white effect.

What is claimed is:

1. A benzoxazolyl-phenyl-stilbene of the formula

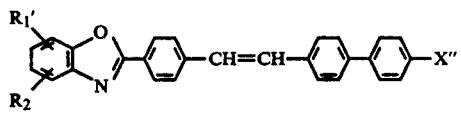

in which $X''$ is cyano, carboxyl, alkoxycarbonyl having 2 to 6 C atoms or alkoxyalkoxycarbonyl having a total of 4 to 7 C atoms, $R_1'$ is hydrogen, alkyl having 1 to 4 C atoms, phenyl, alkoxycarbonyl having 2 to 6 C atoms, alkoxy having 1 to 4 C atoms or chlorine and $R_2$ is hydrogen, alkyl having 1 to 4 C atoms or chlorine.

2. A benzoxazolyl-phenyl-stilbene according to claim 1, of the formula

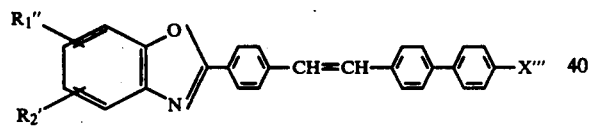

in which $X'''$ is cyano, carboxyl or alkoxycarbonyl having 2 to 6 C atoms, $R_1''$ is hydrogen, alkyl having 1 to 4 C atoms, phenyl, alkoxycarbonyl having 2 to 6 C atoms, chlorine or methoxy and $R_2'$ is hydrogen, methyl, ethyl or chlorine.

3. A benzoxazolyl-phenyl-stilbene according to claim 1, of the formula

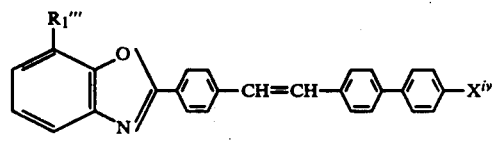

in which $X^{iv}$ is cyano or alkoxycarbonyl having 2 to 5 C atoms and $R_1'''$ is alkyl having 1 to 4 C atoms or methoxy.

4. A process for the preparation of a benzoxazolyl-phenyl-stilbene of the formula

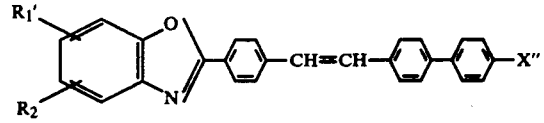

in which $X''$ is cyano, carboxyl, alkoxycarbonyl having 2 to 6 C atoms or alkoxyalkoxycarbonyl having a total of 4 to 7 C atoms, $R_1'$ is hydrogen, alkyl having 1 to 4 C atoms, phenyl, alkoxycarbonyl having 2 to 6 C atoms, methoxy or chlorine and $R_2$ is hydrogen, alkyl having 1 to 4 C atoms or chlorine, which comprises reacting a compound of the formula

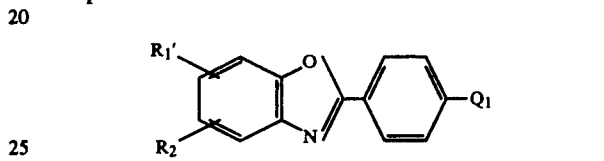

in the presence of a strong base with a compound of the formula

in which formulae $R_1'$, $R_2$ and $X''$ are as defined above and one of the symbols $Q_1$ and $Q_2$ is a —CHO group and the other is a grouping of the formula

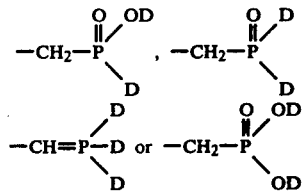

in which D is an unsubstituted or substituted alkyl, aryl, cycloalkyl or aralkyl radical.

5. A process for the fluorescent brightening of natural and synthetic organic materials, which comprises the incorporation in or application to these materials of 0.005 to 2% of one of the benzoxazolyl-phenyl-stilbenes defined in claim 1.

6. A process according to claim 5, for the fluorescent brightening of polyesters, polyvinyl chloride and polyamides.

* * * * *